(12) United States Patent
Ozaki et al.

(10) Patent No.: US 9,168,007 B2
(45) Date of Patent: Oct. 27, 2015

(54) COMPUTER-AIDED DIAGNOSTIC APPARATUS

(75) Inventors: Masahiro Ozaki, Tochigi (JP); Itsuko Iwata, Aichi (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 837 days.

(21) Appl. No.: 10/537,285

(22) PCT Filed: Dec. 2, 2003

(86) PCT No.: PCT/JP03/15443
§ 371 (c)(1),
(2), (4) Date: Jun. 1, 2005

(87) PCT Pub. No.: WO2004/049948
PCT Pub. Date: Jun. 17, 2004

(65) Prior Publication Data
US 2006/0050943 A1    Mar. 9, 2006

(30) Foreign Application Priority Data
Dec. 3, 2002  (JP) ................. 2002-351487

(51) Int. Cl.
*A61B 6/03* (2006.01)
*A61B 6/00* (2006.01)
*G06T 7/00* (2006.01)

(52) U.S. Cl.
CPC .............. *A61B 6/032* (2013.01); *A61B 6/463* (2013.01); *A61B 6/465* (2013.01); *A61B 6/5235* (2013.01); *G06T 7/0012* (2013.01); *G06T 2207/30064* (2013.01)

(58) Field of Classification Search
CPC ........ A61B 6/032; A61B 6/463; A61B 6/465; A61B 6/5235; G06T 7/0012; G06T 2207/30064
USPC ................... 600/407, 411; 382/131
See application file for complete search history.

(56) References Cited

U.S. PATENT DOCUMENTS 5,740,225 A * 4/1998 Nabatame ................ 378/65
5,871,013 A   2/1999 Wainer et al.
(Continued)

FOREIGN PATENT DOCUMENTS

JP    8-320923    12/1996
JP    9-35043     2/1997
(Continued)

OTHER PUBLICATIONS

Ega Aird, et al., "CT simulation for radiotherapy treatment planning", The British Journal of Radiology, 75 (Dec. 2002), pp. 937-949.*

*Primary Examiner* — Katherine Fernandez
(74) *Attorney, Agent, or Firm* — Oblon, McClelland, Maier & Neustadt, L.L.P.

(57) ABSTRACT

A computer aided diagnostic system according to the invention is characterized in that first sick portion detecting means for detecting a sick portion candidate based upon an image acquired by a first modality, second sick portion detecting means for detecting a sick portion candidate based upon an image related to the same region of interest of the same subject and acquired by a second modality different from the modality, detection result synthesizing means for comparing the results of detection by the first and second sick portion detecting means and correspondence displaying means for relating the position of the sick portion candidate detected by the first sick portion detecting means on an image analyzed by the second sick portion detecting means and displaying it and for relating the position of the sick portion candidate detected by the second sick portion detecting means on an image analyzed by the first sick portion detecting means and displaying it are provided. According to the above-mentioned configuration, the computer aided diagnostic system that enables a double check comparing images acquired by plural apparatuses can be provided.

10 Claims, 13 Drawing Sheets

(56) References Cited

U.S. PATENT DOCUMENTS

| | | | | |
|---|---|---|---|---|
| 5,995,581 A * | 11/1999 | Ozaki | | 378/20 |
| 6,075,879 A | 6/2000 | Roehrig et al. | | |
| 6,195,577 B1 * | 2/2001 | Truwit et al. | | 600/411 |
| 6,240,201 B1 * | 5/2001 | Xu et al. | | 382/130 |
| 6,317,617 B1 * | 11/2001 | Gilhuijs et al. | | 600/408 |
| 6,453,058 B1 * | 9/2002 | Murthy et al. | | 382/128 |
| 6,549,645 B1 * | 4/2003 | Oikawa et al. | | 382/132 |
| 6,760,468 B1 * | 7/2004 | Yeh et al. | | 382/132 |
| 6,925,200 B2 * | 8/2005 | Wood et al. | | 382/132 |
| 6,983,063 B1 * | 1/2006 | Novak et al. | | 382/131 |
| 7,072,435 B2 * | 7/2006 | Metz et al. | | 378/8 |
| 7,072,501 B2 * | 7/2006 | Wood et al. | | 382/132 |
| 7,103,205 B2 * | 9/2006 | Wang et al. | | 382/132 |
| 7,295,691 B2 * | 11/2007 | Uppaluri et al. | | 382/130 |
| 7,296,239 B2 * | 11/2007 | Shen et al. | | 715/764 |
| 7,313,259 B2 * | 12/2007 | Alyassin et al. | | 382/128 |

FOREIGN PATENT DOCUMENTS

| | | |
|---|---|---|
| JP | 2003-575 | 1/2003 |
| JP | 2004-159913 | 6/2004 |
| WO | WO 02/34138 A1 | 5/2002 |
| WO | WO 02/43801 A2 | 6/2002 |

* cited by examiner

FIG. 3

| PATIENT NAME | EXAMINATION IDENTIFICATION NUMBER | PHOTO-GRAPHED DATE | IMAGE NUMBER | COORDINATES OF SICK PORTION CANDIDATE | CHARACTER-ISTIC 1 (EFFECTIVE DIAMETER) | CHARACTER-ISTIC 2 (AREA) | CHARACTER-ISTIC 3 (DIAMETER OF CIRCUM-SCRIBED CIRCUIT) | CHARACTER-ISTIC 4 (AREA OF CIRCUM-SCRIBED RECTANGLE) | CHARACTER-ISTIC 5 (CIRCULARITY) | CHARACTER-ISTIC 6 (DEGREE OF UNEVENNESS) |
|---|---|---|---|---|---|---|---|---|---|---|
| PATIENT A | 123456 | 2002. 11. 11 | 6 | (200, 250) | 7 | | | | | |
| PATIENT A | 123456 | 2002. 11. 11 | 10 | (300, 200) | 8 | | | | | |
| PATIENT A | 123456 | 2002. 11. 11 | 17 | (100, 350) | 9 | | | | | |
| PATIENT A | 123456 | 2002. 11. 11 | 21 | (170, 250) | 13 | | | | | |
| PATIENT A | 123456 | 2002. 11. 11 | 22 | (180, 240) | 14 | | | | | |
| PATIENT A | 123456 | 2002. 11. 11 | 23 | (175, 245) | 12 | | | | | |
| PATIENT B | 654321 | 2002. 11. 12 | 15 | (400, 300) | 15 | | | | | |
| PATIENT B | 654321 | 2002. 11. 12 | 16 | (410, 290) | 14 | | | | | |
| PATIENT B | 654321 | 2002. 11. 12 | 24 | (140, 300) | 8 | | | | | |
| ... | ... | ... | ... | ... | ... | ... | ... | ... | ... | ... |

| PATIENT NAME | EXAMINATION IDENTIFICATION NUMBER | PHOTOGRAPHED DATE | COORDINATES OF SICK PORTION CANDIDATE | CHARACTERISTIC 1 (EFFECTIVE DIAMETER) | CHARACTERISTIC 2 (AREA) | CHARACTERISTIC 3 (DIAMETER OF CIRCUMSCRIBED CIRCUIT) | CHARACTERISTIC 4 (AREA OF CIRCUMSCRIBED RECTANGLE) | CHARACTERISTIC 5 (CIRCULARITY) | CHARACTERISTIC 6 (DEGREE OF UNEVENNESS) |
|---|---|---|---|---|---|---|---|---|---|
| PATIENT A | 234567 | 2002.11.10 | (200, 60) | 7 | | | | | |
| PATIENT A | 234567 | 2002.11.10 | (250, 80) | 8 | | | | | |
| PATIENT A | 234567 | 2002.11.10 | (100, 170) | 9 | | | | | |
| PATIENT A | 234567 | 2002.11.10 | (180, 220) | 14 | | | | | |
| PATIENT B | 765432 | 2002.11.12 | (400, 300) | 15 | | | | | |
| PATIENT B | 765432 | 2002.11.12 | (410, 290) | 14 | | | | | |
| PATIENT B | 765432 | 2002.11.12 | (140, 300) | 8 | | | | | |
| ... | ... | ... | ... | ... | ... | ... | ... | ... | ... |

FIG. 6

| DATA NUMBER | PATIENT NAME | CT ||||| X-TV |||| |
|---|---|---|---|---|---|---|---|---|---|---|
| | | EXAMINATION IDENTIFICATION NUMBER | PHOTOGRAPHED DATE | IMAGE NUMBER | COORDINATES OF SICK PORTION CANDIDATE | CHARACTERISTIC 1 (EFFECTIVE DIAMETER) | EXAMINATION IDENTIFICATION NUMBER | PHOTOGRAPHED DATE | COORDINATES OF SICK PORTION CANDIDATE | CHARACTERISTIC 1 (EFFECTIVE DIAMETER) |
| 1 | PATIENT A | 123456 | 2002. 11. 11 | 6 | (200, 250) | 7 | 234567 | 2002. 11. 10 | (200, 60) | 7 |
| 2 | | | | | | | 234567 | 2002. 11. 10 | (250, 80) | 8 |
| 3 | PATIENT A | 123456 | 2002. 11. 11 | 10 | (300, 200) | 8 | | | | |
| 4 | PATIENT A | 123456 | 2002. 11. 11 | 17 | (100, 350) | 9 | 234567 | 2002. 11. 10 | (100, 170) | 9 |
| 5 | PATIENT A | 123456 | 2002. 11. 11 | 21 | (170, 250) | 13 | | | | |
| 6 | PATIENT A | 123456 | 2002. 11. 11 | 22 | (180, 240) | 14 | 234567 | 2002. 11. 10 | (180, 220) | 14 |
| 7 | PATIENT A | 123456 | 2002. 11. 11 | 23 | (175, 245) | 12 | | | | |
| 8 | PATIENT B | 654321 | 2002. 11. 12 | 15 | (400, 300) | 15 | 765432 | 2002. 11. 12 | (400, 300) | 15 |
| 9 | PATIENT B | 654321 | 2002. 11. 12 | 16 | (410, 290) | 14 | 765432 | 2002. 11. 12 | (410, 290) | 14 |
| 10 | PATIENT B | 654321 | 2002. 11. 12 | 24 | (140, 300) | 8 | 765432 | 2002. 11. 12 | (140, 300) | 8 |
| ... | ... | | | | | | | | | |

FIG. 9

| DATA NUMBER | PATIENT NAME | CT | | | | | X-TV | | | |
|---|---|---|---|---|---|---|---|---|---|---|
| | | EXAMINATION IDENTIFICATION NUMBER | PHOTOGRAPHED DATE | IMAGE NUMBER | COORDINATES OF SICK PORTION CANDIDATE | CHARACTERISTIC 1 (EFFECTIVE DIAMETER) | EXAMINATION IDENTIFICATION NUMBER | PHOTOGRAPHED DATE | COORDINATES OF SICK PORTION CANDIDATE | CHARACTERISTIC 1 (EFFECTIVE DIAMETER) |
| 1 | PATIENT A | 123456 | 2002.11.11 | 6 | (200, 250) | 7 | 234567 | 2002.11.10 | (200, 60) | 7 |
| 2 | | 123456 | 2002.11.11 | | | 8 | 234567 | 2002.11.10 | (250, 80) | 8 |
| 3 | PATIENT A | 123456 | 2002.11.11 | 10 | (300, 200) | 9 | | | | |
| 4 | PATIENT A | 123456 | 2002.11.11 | 17 | (100, 350) | 13 | 234567 | 2002.11.10 | (100, 170) | 9 |
| 5 | PATIENT A | 123456 | 2002.11.11 | 21 | (170, 250) | 14 | | | | |
| 6 | PATIENT A | 123456 | 2002.11.11 | 22 | (180, 240) | 12 | 234567 | 2002.11.12 | (180, 220) | 14 |
| 7 | PATIENT A | 123456 | 2002.11.11 | 23 | (175, 245) | 15 | | | | |
| 8 | PATIENT B | 654321 | 2002.11.12 | 15 | (400, 300) | 14 | 765432 | 2002.11.12 | (400, 300) | 15 |
| 9 | PATIENT B | 654321 | 2002.11.12 | 16 | (410, 290) | 8 | 765432 | 2002.11.12 | (410, 290) | 14 |
| 10 | PATIENT B | 654321 | 2002.11.12 | 24 | (140, 300) | | 765432 | 2002.11.12 | (140, 300) | 8 |

FIG. 14A
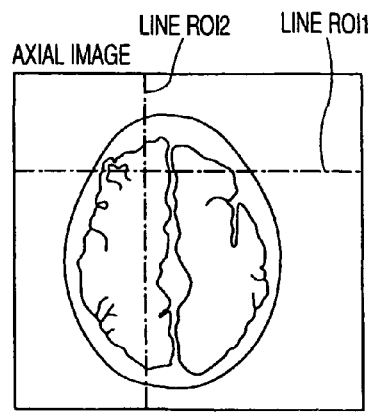
FIG. 14B
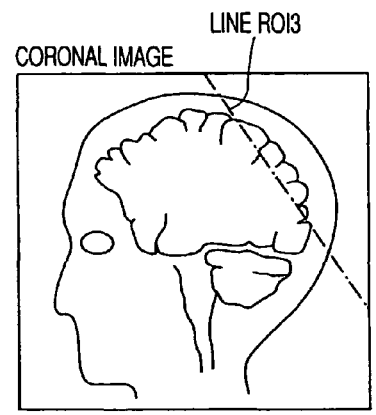
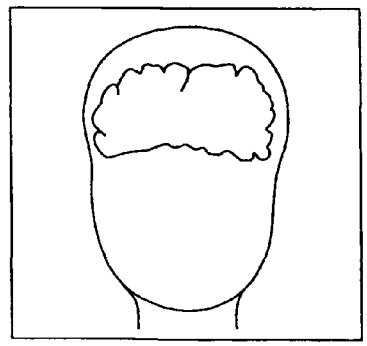
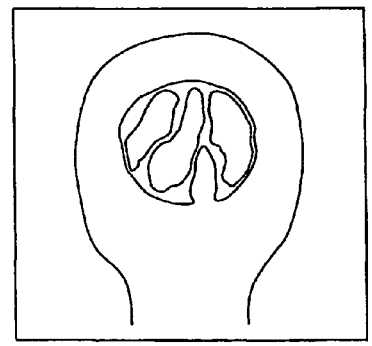
FIG. 14C
FIG. 14D

COMPUTER-AIDED DIAGNOSTIC APPARATUS

TECHNICAL FIELD

The present invention relates to a computer aided diagnostic system for aiding diagnosis using an image for medical application, particularly relates to a computer aided diagnostic system for analyzing plural types of images according to image processing algorithm suitable for respective types by a computer and enabling utilizing them for enhancing the efficiency and reliability of interpreting a shadow by comparing and contrasting acquired abnormality information.

BACKGROUND ART

Recently in a medical spot, diagnosis using an imaging diagnostic system (hereinafter called a modality) represented by an X-ray computerized tomograph (X-ray CT), an ultrasonic diagnostic system and a magnetic resonance imaging (MRI) system is frequently performed. Further currently, computer aided detection (CAD) using these is also frequently used (for example, refer to JP-3083606).

The computer aided diagnostic system is a system for automatically extracting sick portions and outputting the features of normal and abnormal patterns to aid diagnosis by a doctor for interpreting a shadow. It automates detection work by programming a diagnostic rule by the doctor for interpreting a shadow and reduces a load of the doctor for interpreting a shadow. The doctor for interpreting a shadow finally classifies whether a detected sick portion is a tumor or not or whether it is benign or malignant based upon the output result. Computer aided diagnosis including this classification in the computer aided detection described above is also called CAD.

For the object of such computer aided detection, in addition to automatic diagnosis and labor saving in screening, it can be given to prevent oversight by a doctor. A conventional type radioscopic method in X-ray direct photography and an X-ray TV apparatus has a defect that as information is integrated in a direction of the thickness, contrast is hardly acquired and even if there is a fault, its position in the direction of the thickness cannot be known. For example, a tumor located at the back of the heart and a tumor located at the apex of a lung are difficult to discover in the above-mentioned radioscopic method. In the meantime, also in X-ray CT without such a defect, some tumors may look like a blood vessel at a glance and there may be unexpected oversight.

For such oversight, as CAD is basically acquired by programming a diagnostic rule of a doctor for interpreting a shadow, the similar oversight is estimated even according to CAD.

To prevent such oversight, a system for comparing the result of CAD and a report on the interpretation of a shadow by a doctor and issuing warning in case there is difference between both (for example, refer to JP-3085724) and a system for enhancing the precision of diagnosis by comparing the current image and a past image (for example, refer to JP-A-2001-137230) are proposed.

To prevent such oversight and to enhance the reliability of diagnosis based upon an image, a double check by comparing images acquired in plural systems is more desirable. However, this imposes a double load on a doctor for interpreting a shadow. Besides, at least two types of images are required to be compared, however, two types of results of diagnosis are not always acquired.

The invention is made in view of the above-mentioned situation and the object is to provide a computer aided diagnostic system that enhances the reliability of diagnosis based upon an image and does not impose an excess load on a doctor for interpreting a shadow.

Another object of the invention is to provide a computer aided diagnostic system provided with a function for enabling diagnosis of two types based upon only an image for medical application acquired in one modality.

DISCLOSURE OF THE INVENTION

A computer aided diagnostic system according to the invention is characterized in that to solve the above-mentioned problem, it is provided with sick portion detecting means for detecting a sick portion candidate based upon an image acquired by one modality and correspondence displaying means for relating the position of the detected sick portion candidate on an image acquired by second modality different from the first modality and displaying it.

Hereby, as the sick portion candidate detected according to one algorithm is displayed with the candidate superimposed on the image of a different type, it can be checked whether the sick portion candidate also exists on the image or not.

Desirably, the computer aided diagnostic system according to the invention is provided with first sick portion detecting means for detecting a sick portion candidate based upon an image acquired by a first modality, second sick portion detecting means for detecting a sick portion candidate based upon an image related to the same region of interest of the same subject and acquired by the second modality different from the first modality and detection result synthesizing means for comparing and contrasting the results detected by the first and second sick portion detecting means.

Besides desirably, the computer aided diagnostic system according to the invention may be also provided with correspondence displaying means for relating the position of a sick portion candidate detected by the first sick portion detecting means on an image analyzed by the second sick portion detecting means and displaying it and for relating the position of a sick portion candidate detected by the second sick portion detecting means on an image analyzed by the first sick portion detecting means and displaying it.

By these, as the sick portion candidates are detected based upon images acquired by plural modalities according to plural algorithm and are compared or are superimposed and displayed on another image, the double check of the sick portion candidate is facilitated.

Further desirably, the computer aided diagnostic system according to the invention is provided with correspondence displaying means for displaying the following portion so that the portion can be identified in case the detection result synthesizing means judges that there is the portion detected as a sick portion candidate by only either of the first or second sick portion detecting means.

Such a computer aided diagnostic system is applied to a case that an image acquired in either of the first or second modality is an X-ray CT image and an image acquired in the other modality is a simple X-ray radioscopic image for example.

Besides, the computer aided diagnostic system according to the invention is provided with sick portion detecting means for detecting a sick portion candidate based upon an image acquired by one modality, image transforming means for transforming the image acquired by the modality and correspondence displaying means for relating the position of the sick portion candidate detected by the sick portion detecting means on the transformed image and displaying it as another embodiment.

Or the computer aided diagnostic system according to the invention may be also provided with image transforming means for transforming an image acquired by one modality, sick portion detecting means for detecting a sick portion candidate based upon the transformed image and correspondence displaying means for relating the position of the sick portion candidate detected by the sick portion detecting means on the image acquired by the modality and displaying it.

As described above, a sick portion candidate detected according to one algorithm can be superimposed and displayed on an image of a different type by transforming the following image based upon only the image acquired from one modality.

Desirably, the computer aided diagnostic system according to the invention may be also provided with first sick portion detecting means for detecting a sick portion candidate based upon an image acquired by one modality, image transforming means for transforming the image acquired by the modality, second sick portion detecting means for detecting a sick portion candidate based upon the transformed image and detection result synthesizing means for comparing and contrasting the results of detection by the first and second sick portion detecting means.

Besides desirably, correspondence displaying means for relating the position of a sick portion candidate detected by the first sick portion detecting means on an image analyzed by the second sick portion detecting means and displaying it and for relating the position of a sick portion candidate detected by the second sick portion detecting means on an image analyzed by the first sick portion detecting means and displaying it can be also provided.

Further desirably, the computer aided diagnostic system according to the invention is provided with correspondence displaying means for displaying the following portion so that the portion can be identified in case the detection result synthesizing means judges that there is the portion detected as a sick portion candidate by only either of the first or second sick portion detecting means.

For one example, such a computer aided diagnostic system is applied to a case that the image acquired by the modality is an X-ray CT image and the image generated by the image transforming means is a simple X-ray radioscopic image as in the above-mentioned case.

Besides, the computer aided diagnostic system according to the invention is provided with sick portion detecting means for detecting a sick portion candidate based upon an image acquired by a modality which can sense plural tomographic images, image reconfiguring means for reconfiguring an image based upon stereoscopic image data acquired by the modality and correspondence displaying means for relating the position of the sick portion candidate detected by the sick portion detecting means on the reconfigured image and displaying it as further another embodiment.

Or the computer aided diagnostic system according to the invention may be also provided with image reconfiguring means for reconfiguring an image based upon stereoscopic image data acquired by a modality which can sense plural tomographic images, sick portion detecting means for detecting a sick portion candidate based upon the reconfigured image and correspondence displaying means for relating the position of the sick portion candidate detected by the sick portion detecting means on the image acquired by the modality and displaying it.

As described above, a sick portion candidate detected according to one algorithm can be also superimposed and displayed on an image of a different type by reconfiguring an image based upon only the image acquired by one modality.

Desirably, first sick portion detecting means for detecting a sick portion candidate based upon an image acquired by a modality which can sense plural tomographic images, image reconfiguring means for reconfiguring an image based upon stereoscopic image data acquired by the modality, second sick portion detecting means for detecting a sick portion candidate based upon the reconfigured image and detection result synthesizing means for comparing and contrasting the results of detection by the first and second sick portion detecting means may be also provided.

Besides desirably, correspondence displaying means for relating the position of a sick portion candidate detected by the first sick portion detecting means on an image analyzed by the second sick portion detecting means and displaying it and for relating the position of a sick portion candidate detected by the second sick portion detecting means on an image analyzed by the first sick portion detecting means and displaying it can be also provided.

Further desirably, correspondence displaying means for displaying the following portion so that the portion can be identified in case the detection result synthesizing means judges that there is the portion detected as a sick portion candidate by only either of the first or second sick portion detecting means is provided.

For one example, such a computer aided diagnostic system is applied to a case that the modality is X-ray CT, the image analyzed by the sick portion detecting means is plural axial images reconfigured by the X-ray CT and the image reconfiguring means generates a projected image based upon the plural axial images.

Besides, for example, such a computer aided diagnostic system is applied to a case that the modality is X-ray CT, the image analyzed by the sick portion detecting means is plural axial images reconfigured by the X-ray CT and the image reconfiguring means generates an MPR image based upon the plural axial images.

BRIEF DESCRIPTION OF THE DRAWINGS

FIG. 3 shows the configuration of a sick portion candidate information table stored in a first detection result storage shown in FIG. 1;

FIG. 5 shows the configuration of a sick portion candidate information table stored in a second detection result storage shown in FIG. 1;

FIG. 6 shows the configuration of a sick portion candidate information table stored in a synthesized detection result storage shown in FIG. 1;

FIG. 9 shows an example of the display of detection results in case a sick portion is detected based upon a simple X-ray image and no sick portion is detected based upon an X-ray CT image;

FIG. 10 are explanatory drawings for explaining the change of the size of a marker showing a sick portion.

FIG. 14 are explanatory drawings for explaining an MPR image, FIG. 14A shows an axial image, FIG. 14B shows a coronal image, FIG. 14C shows a sagittal image, and FIG. 14D shows an oblique image.

BEST MODE FOR CARRYING OUT THE INVENTION

Referring to the attached drawings, a first embodiment of a computer aided diagnostic system according to the invention will be described below.

Figure 1:
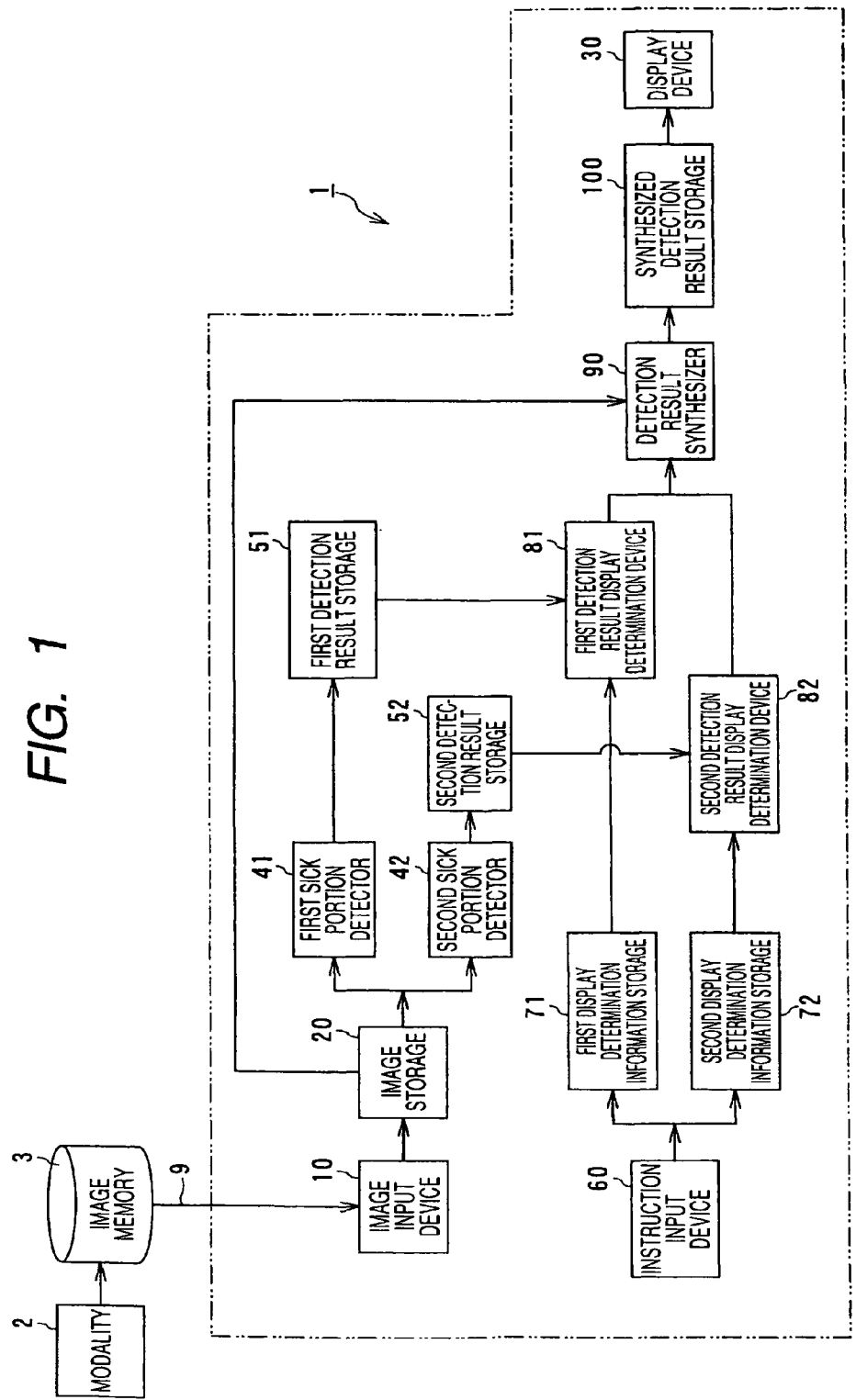
FIG. 1 is a block diagram showing the outline of a function of a computer aided diagnostic system equivalent to a first embodiment of the invention.

FIG. 1 is a block diagram showing the outline of a function of the computer aided diagnostic system (a CAD system) 1 equivalent to the first embodiment. An arrow between blocks denotes the flow of main data.

In the CAD system 1 equivalent to this embodiment, main data input via two input devices, that is, an image input device 10 and an instruction input device 60 is substantially transmitted to first detecting means and second detecting means by grouping the data and after the main data is synthesized by detection result synthesizing means, it is displayed on a display device 30 for displaying the result of detection. In this embodiment, the first detecting means processes and detects an X-ray CT image and the second detecting means processes and detects a simple X-ray image. The above-mentioned simple X-ray image means an X-ray radioscopic image acquired by an X-ray TV apparatus and a traditional X-ray machine.

The first detecting means includes a first sick portion detector 41, a first detection result storage 51, a first display determination information storage 71 and a first display determination device 81 as shown in FIG. 1. Similarly, the second detecting means includes a second sick portion detector 42, a second detection result storage 52, a second display determination information storage 72 and a second display determination device 82. The detection result synthesizing means includes a detection result synthesizer 90 and a synthesized detection result storage 100.

The CAD system 1 is provided with an image storage 20 immediately after the image input device 10 in addition to the above-mentioned and is also provided with a controller (not shown) for controlling the motion of the whole system.

The image input device 10 is connected to a network 9 and is provided with a function as an interface for inputting an image for medical application transferred directly from a modality 2 such as X-ray CT and an MRI system or via an image memory 3 such as a picture archiving and communication system (PACS) via the network 9. The image storage 20 is equipped with a storage medium such as a mass magnetic disk and a photomagnetic disk so as to store the data of an image for medical application input from the image input device 10. This CAD system 1 may be also configured as an independent type system which is not connected to a network and in which image information is input to the image storage 20 via a record medium.

The first and second sick portion detectors 41, 42 are provided to process an image for medical application stored in the image storage 20 according to the existing general arbitrary algorithm, to detect an abnormal shadow included in the image for medical application as a candidate of a sick portion and to calculate area and others which are the respective modal characteristics of detected sick portion candidates.

This algorithm is different depending upon a type of a sensed internal organ and is also different depending upon a used modality. Therefore, as first and second images of different types for the same portion are generated and different algorithm of first algorithm for the first image and second algorithm for the second image is applied, a lesion can be doubly checked according to completely different diagnostic rules.

As for this algorithm, for example, as for algorithm in relation to a field of a lung, there are minute calcification detection algorithm, interstitial lung malady detection algorithm, lung nodule detection algorithm or lung cancer detection algorithm and they are used according to the purpose of detection. In case there are plural purposes of detection, analysis according to another algorithm is made after analysis according to one algorithm.

The first and second detection result storages 51, 52 are provided to relate the position on an image of each sick portion candidate detected by the first and second sick portion detectors 41, 42 and calculated modal characteristics to a name of a patient, an examination identification number, an image number and others and to store them in sick portion candidate information tables A, B (see FIGS. 3 and 5).

The first and second detection result display determination devices 81, 82 are provided to determine and select a sick portion candidate to be displayed (a specific sick portion candidate) out of all sick portion candidates detected by the first and second sick portion detectors 41, 42 according to display determination reference information stored on a storage medium such as a magnetic disk of the first and second display determination information storages 71, 72. A doctor for interpreting a shadow can freely change or set a criterion for display determination by operating various input equipment such as a mouse, a keyboard and a touch panel equipped in the instruction input device 60.

The detection result synthesizer 90 is provided with an image matching function and a detection result comparison function, compares the positions of specific sick portion candidates respectively determined to be displayed and selected by the detection result display determination devices 81, 82, and identifies whether both are the same or not.

The image matching function represents the same positions and the same size on an X-ray CT image and a simple X-ray image on the same coordinate axes by coordinate transformation such as affine transformation, enables the comparison of both images, and can also match them on a simple X-ray image on a coronal face and on a multisliced tomographic image on an axial face.

The detection result comparison function identifies the position of a specific sick portion candidate determined to be displayed and selected on the X-ray CT image and the simple X-ray image which are made equal in size and a position by the image matching function by comparing numerals showing the position on coordinate axes.

The synthesized detection result storage 100 contrasts the position and the calculated modal characteristics of the sick portion candidate identified by the detection result synthesizer 90 and those of a sick portion detected only on one image and unidentified with sick portion candidates detected by the first sick portion detector 41 and by the second sick portion detector 42 as shown in FIG. 6, relates them to the name of the patient, the examination identification number, the image number and others, and stores them as a sick portion candidate information table C.

The display device 30 is provided with display equipment such as a cathode ray tube (CRT) and a liquid crystal display, displays images for medical application read from the image storage 20 to analyze them in the first and second detecting means in parallel, and presents the position of a specific sick portion candidate determined to be displayed and selected by the first and second detection result display determination devices 81, 82 on the image for medical application by superimposing a mark on the coordinates of the sick portion candidate. This mark is displayed by reflecting the result compared by the detection result synthesizer 90 on both images. Besides, the display device 30 can also instruct the display equipment to display the position of a specific sick portion candidate determined to be displayed and selected by the first and second detection result display determination devices 81, 82 in the form of sick portion candidate information tables A, B.

Figure 2:
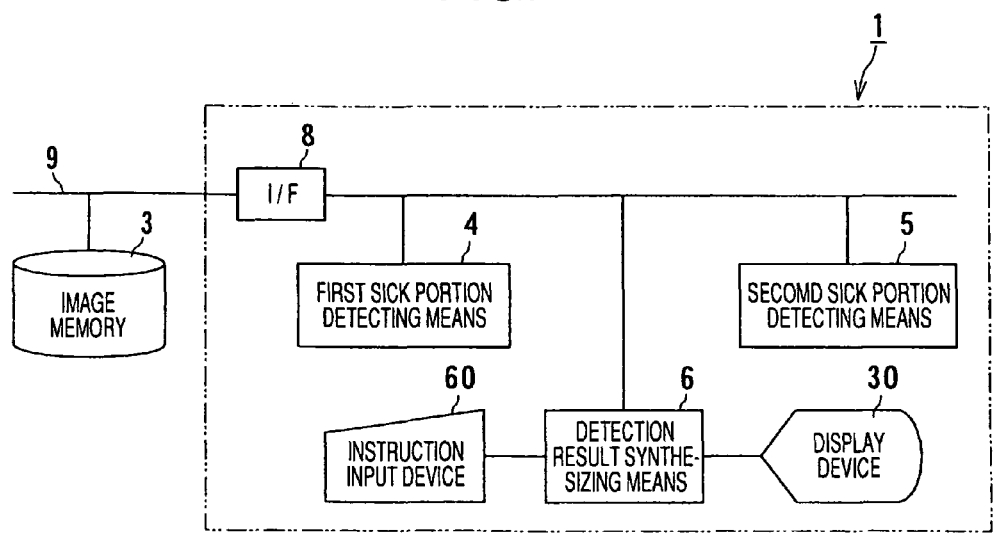
FIG. 2 is a block diagram showing an example of the configuration of the computer aided diagnostic system equivalent to the first embodiment of the invention.

FIG. 2 shows one example of the configuration of the CAD system 1 that realizes the above-mentioned functions. As shown in FIG. 2, the CAD system 1 includes an interface (I/F) 8, first sick portion detecting means 4, second sick portion detecting means 5, detection result synthesizing means 6, an instruction input device 60 and the display device 30. The instruction input device 60 and the display device 30 are the same as those shown in FIG. 1, I/F 8 is equivalent to the image input device 10 and the image storage 20 shown in FIG. 1 and is connected to the image memory 3 via the network 9.

The first sick portion detecting means 4 is provided with the functions of the first sick portion detector 41, the first detection result storage 51, the first display determination information storage 71 and the first display determination device 81 respectively shown in FIG. 1, and similarly, the second sick portion detecting means 5 is provided with the functions of the second sick portion detector 42, the second detection result storage 52, the second display determination information storage 72 and the second display determination device 82. Further, the detection result synthesizing means 6 fulfills the functions of the detection result synthesizer 90 and the synthesized detection result storage 100.

The display device 30 realizes the correspondence displaying means according to the invention.

The first sick portion detecting means 4, the second sick portion detecting means 5 and the detection result synthesizing means 6 are a workstation including CPU, ROM, RAM and an auxiliary storage and particularly, the detection result synthesizing means 6 can also function as a controller.

Next, the operation of the CAD system 1 configured as described above, that is, operation since image data is input until the result of detection is stored via a process for detecting a sick portion candidate and the results of detection are synthesized will be described for an example that lung cancer candidates are detected based upon a chest X-ray CT image and a chest X-ray radioscopic image and the results of detection are compared and displayed.

First, image data transferred on the network from X-ray CT and image data transferred on the network from an X-ray TV apparatus reach the image input device 10. The image from the X-ray TV apparatus may be also image data acquired by digitizing a film photographed by a traditional X-ray machine by a film digitizer. These image data are transmitted to the image storage 20 and are stored in it. The image data includes image incidental information such as a name of a patient, an examination identification number and an image number and the distribution of a CT value (a pixel value).

Image data stored in the image storage 20 is read according to control by the controller, one X-ray CT image is sent to the first sick portion detector 41, and one simple X-ray image is sent to the second sick portion detector 42. The sick portion detectors 41, 42 execute a process for detecting a lung cancer candidate according to respective algorithm when they receive image data. Its procedure includes a step 1 for extracting a lung field from the chest X-ray CT image or the simple X-ray image, a step 2 for extracting a region having a larger pixel value by the processing of a threshold in the extracted lung field, a step 3 for operating the characteristics such as circularity of the extracted region having the larger pixel value and a step 4 for specifying a sick portion candidate based upon the characteristics, operating the center of the gravity of the region and specifying the position.

When a lung cancer candidate detection process for one subject is finished in the first and second sick portion detectors 41, 42, image incidental information, the coordinates of the detected lung cancer candidate, the data of calculated modal characteristics are sent to the first and second detection result storages 51, 52 and are stored in them. For these modal characteristics, for example, the effective diameter of an abnormal shadow region of a lung cancer candidate (a diameter of a circle having the same area as that of the abnormal shadow region of the lung cancer candidate), the area of the abnormal shadow region, a diameter of a circumscribed circle, the area of a circumscribed rectangle, circularity and a degree of the unevenness of a margin are conceivable.

The image incidental information, the coordinates of the lung cancer candidate and the characteristics are supplied from the first sick portion detector 41 to the first detection result storage 51, the name of the patient, the examination identification number, the image number and others are extracted from the image incidental information, are registered and stored in the sick portion candidate information table A together with the coordinates of each lung cancer candidate and characteristic data. FIG. 3 shows an example of the contents of the stored sick portion candidate information table A. FIG. 3 shows that first six lines show that each lung cancer candidate region is detected based upon six images for the examination having an examination identification number "123456" of the patient, "Patient A".

Figure 4:
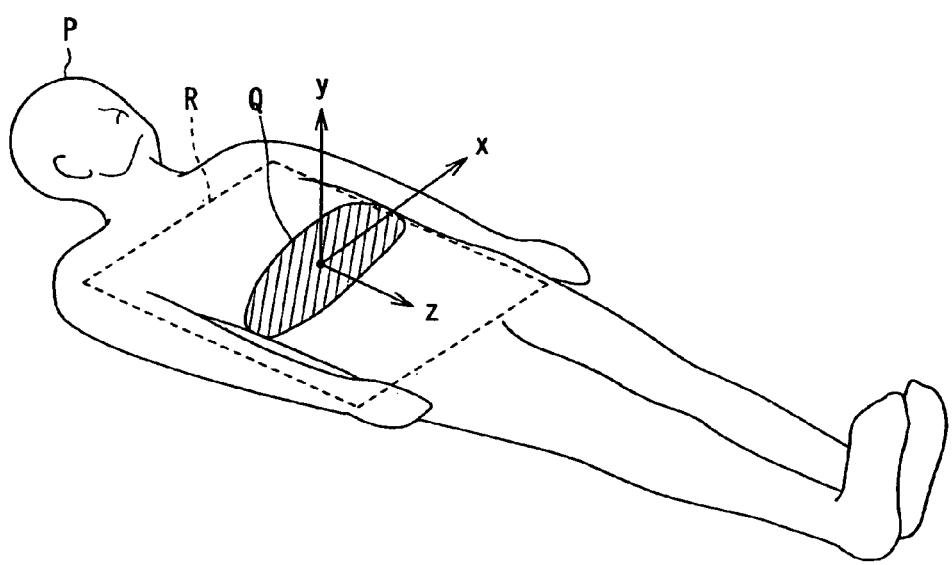
FIG. 4 is an explanatory drawing for explaining relation among the coordinates of a sick portion candidate.

Referring to FIG. 4 showing coordinate relation, "the coordinates of the sick portion candidate" in the sick portion candidate information table A shown in FIG. 3 will be described below. As shown in FIG. 4, P denotes an examined body, Q denotes one image of multisliced tomographic images sensed and reconfigured by the X-ray CT, and R denotes an X-ray radioscopic image. For example, in the case of a so-called helical CT scan that the collection of digitally reconstructed data is repeated while an X-ray tube draws a helical orbit for the examined body, approximately 35 pieces of helical CT images reconfigured with the linear interpolation of 180° and at an interval of 10 mm, having the size of 512×512 pixels, having the gradation of 12 bits per pixel and ranging from the upside to the downside in the whole lung field are collected.

The position on the x-coordinate and the y-coordinate of the X-ray CT tomographic image Q is represented as (x, y) in the item of "the coordinates of a sick portion candidate" and the position on the z-axis is represented by its image number.

That is, in case an interval between multisliced tomographic images is 10 mm, a z-axis coordinate value of an image number 10 is 100 mm.

Similarly, image incidental information, the coordinates of a lung cancer candidate and characteristics are supplied from the second sick portion detector 42 to the second detection result storage 52, a name of a patient, an examination identification number, an image number and others are extracted from the image incidental information, they are registered and stored in the sick portion candidate information table B together with the coordinates of each lung cancer candidate and characteristic data. FIG. 5 shows an example of the stored contents of the sick portion candidate information table B. "The coordinates of a sick portion candidate" in the sick portion candidate information table B shown in FIG. 5 shows the position (x, z) on the x-coordinate and the z-coordinate. As a simple X-ray radioscopic image R is a two-dimensional digitally reconstructed radiograph as shown in FIG. 4, it has no information in a direction of the y-axis.

The sick portion candidate information tables A, B are used for identifying a lung cancer candidate transmitted to the detection result synthesizer 90 and detected by the first and second sick portion detectors 41, 42. For preparation for it, adjustment that "the coordinates of a sick portion candidate" are matched is made by the image matching function. This adjustment is made by measuring similarity between two signals of two images based upon a longitudinal center line and the coordinates on the image of anatomical conformity (a landmark) in respective right and left lungs such as the lower margin of a clavicle, the upper margin of a diaphragm and the position of a rib.

Both cannot be compared by the detection result comparison function until "the coordinates of a sick portion candidate" in the sick portion candidate information tables A, B are displayed on the same coordinate axes as shown in FIG. 4 by the image matching function. The detection result comparison function compares values of "the coordinates of a sick portion candidate" in the sick portion candidate information tables A, B and determines whether the sick portion candidates are the same lung cancer candidate or not. The result of the comparison is transmitted to the synthesized detection result storage 100 and is stored in it. FIG. 6 shows an example of the stored contents of the sick portion candidate information table C. The contents of "CT" on the upside of the left side of the sick portion candidate information table C are extracted from the table A as a lung cancer candidate as a result of detection on an X-ray CT image and the contents of "X-TV" on the upside of the right side are extracted from the table B as a result of detection on a simple X-ray image. In case it is determined that lung cancer candidates detected by the first and second sick portion detectors 41, 42 are the same, the lung cancer candidates are displayed side by side on the sick portion candidate information table C as shown in FIG. 6. Lung cancer candidates in fixed tolerance are also regarded as the same, however, the tolerance can be changed by a doctor for interpreting a shadow. In the case of a lung cancer candidate detected by only either of the first or second sick portion detector 41, 42, that is, in case data to be related are not recognized, the undetected other remains blank.

Figure 7:
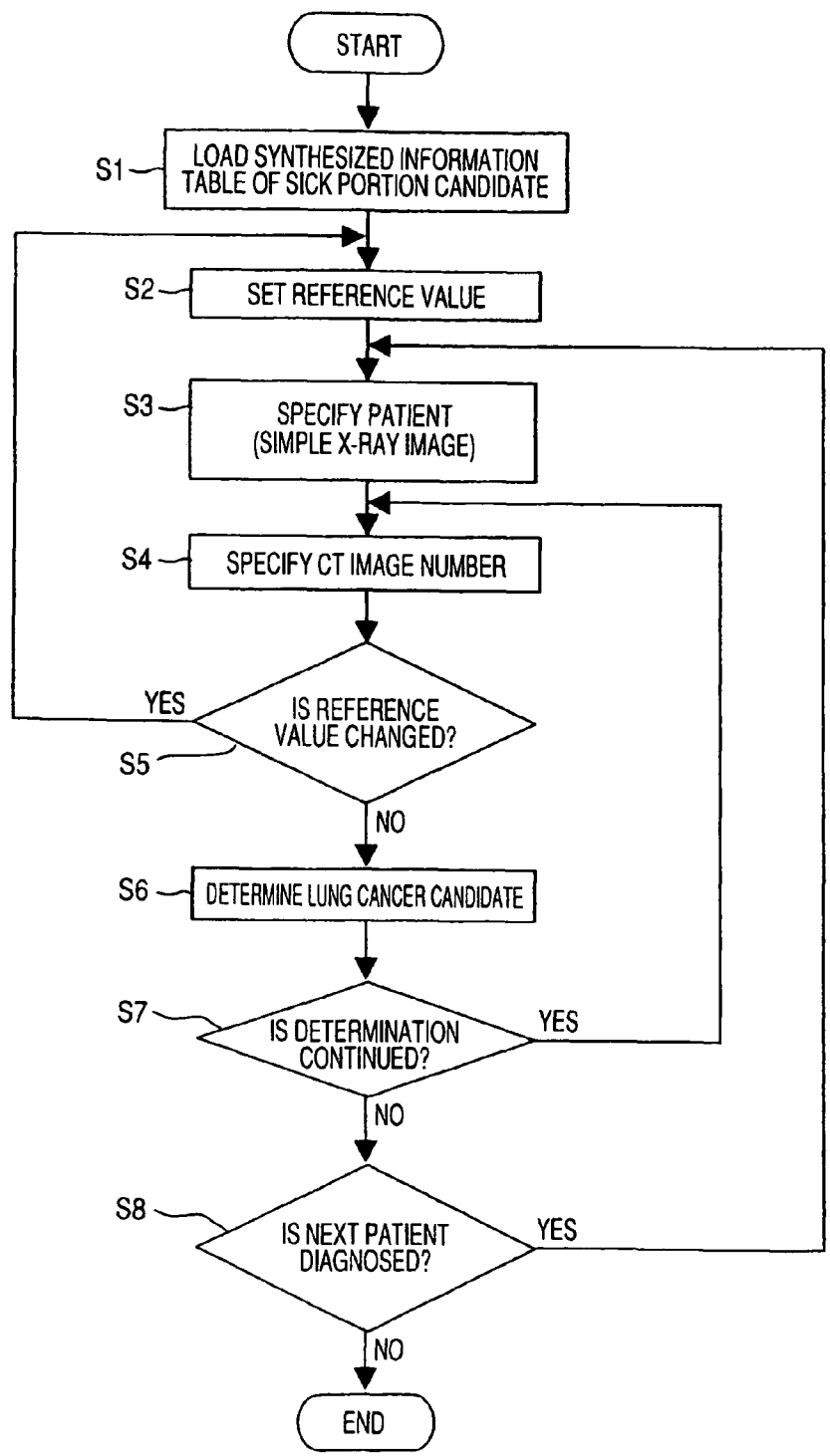
FIG. 7 is a flowchart showing the outline of a procedure for operation for interpreting a shadow.

Next, referring to FIG. 7, the operation of a doctor for interpreting a shadow who interprets a shadow on an image based upon information acquired as described above using the CAD system 1 will be described.

First, when the doctor inputs a request for displaying the result of the detection of a lung cancer candidate via the instruction input device 60, the sick portion candidate information table C stored in the synthesized detection result storage 100 is loaded onto the controller and is displayed on the display 30 (a step S1).

Next, a screen for changing an initial value of display determination reference information and a value of each display determination reference information respectively stored in the first and second display determination information storages 71, 72 is displayed on the touch panel. This screen is realized by a well-known graphic user interface and a reference value for display determination can be arbitrarily set or changed (a step S2).

Figure 8:
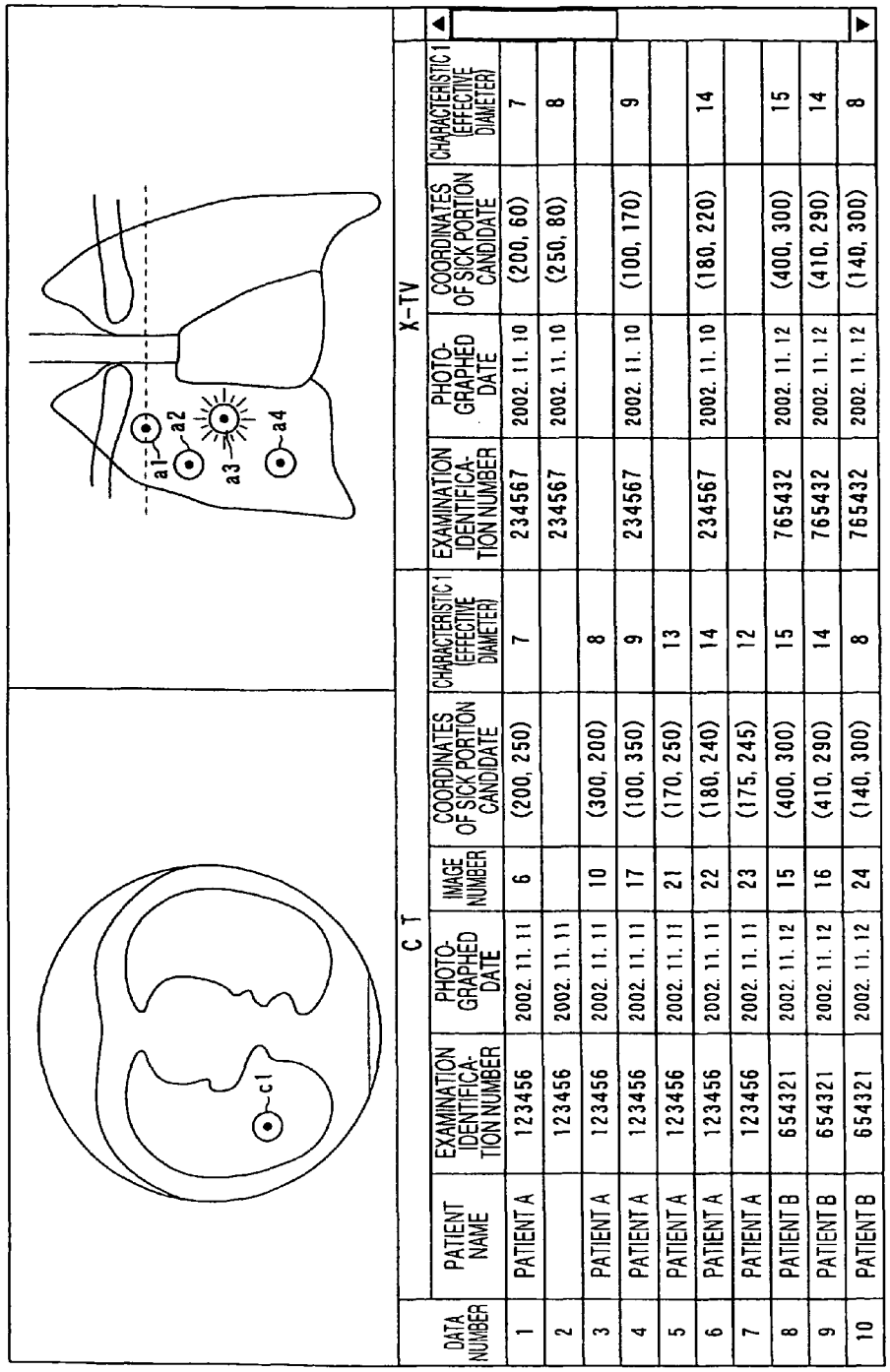
FIG. 8 shows an example of the display of detection results in case a sick portion is detected based upon an X-ray CT image and no sick portion is detected based upon a simple X-ray image.

The display determination reference information is read from the first and second display determination information storages 71, 72 by the first and second detection result display determination devices 81, 82 according to the instruction of the controller. The display determination reference information is sent to the detection result display determination devices 81, 82 every change (a step S5). FIG. 8 shows an example of display on the display 30 when a shadow is interpreted, however, at this stage, only the sick portion candidate information table C is displayed in a lower part.

Next, the doctor interprets a shadow according to the following procedure. In this case, the doctor interprets the result of the detection of the patient "Patient A".

The doctor selects the patient "Patient A" in the sick portion candidate information table C already displayed on the display 30 (a step S3). This selection can be also made by pointing an examination identification number "234567" of a simple X-ray image on the screen via a mouse of the instruction input device 60 and doubly clicking the mouse (see FIG. 8). When the selection of the patient is input, the controller controls so that the simple X-ray image equivalent to the examination identification number "234567" is called from the image storage 20 and is displayed. As a simple X-ray image is one per one patient as a rule, it is not changed while a shadow related to the same patient is interpreted.

When the patient is specified, the controller controls so that an X-ray CT image for comparing with the simple X-ray image is called from the image storage 20 and is displayed (a step S4). As the approximately 35 X-ray CT images exist per one patient, they are displayed in the order of a smaller image number having the information of a lung cancer candidate as a rule. Or the image for interpreting a shadow can be also selected by pointing the image number of the X-ray CT image on the screen via the mouse of the instruction input device 60 and doubly clicking the mouse (see FIG. 8). One X-ray CT image is displayed one by one on the display 30.

When the first and second detection result display determination devices 81, 82 receive the sick portion candidate information of an image number 6 (or a selected image number) of examination having the examination identification number "123456" or the sick portion candidate information of examination having the examination identification number "234567" respectively sent from the first and second detection result storages 51, 52 and display determination reference information sent from the first and second display determination information storages 71, 72, they compare a display determination criterion and characteristics included in the sick portion candidate information every individual display determination criterion (a step S6). Modal characteristics used for the display determination criterion may be also one type and two types or more may be also arbitrarily combined.

It is determined whether the sick portion candidate included in the sick portion candidate information is included in a range of display determination reference values or not. In the determination, sick portion candidates in the range of the display determination reference values are selected as an object of display and those outside the range are removed from the object of display.

The sick portion candidates selected as the object of display as described above are displayed by circular marks a1 to a4 and c1 respectively showing the position on the X-ray CT image and the simple X-ray image on the display 30 as shown in FIG. 8. Hereby, as the sick portion candidates are focused, oversight by the doctor can be reduced. In this case, on the simple X-ray image, all sick portion candidates of the patient are marked, however, on the X-ray CT image, only the sick portion candidate included in the tomographic image is displayed. For example, when the sick portion candidate a1 on the simple X-ray image shown in FIG. 8 is interpreted, an X-ray CT image having an image number including a sick portion candidate corresponding to the sick portion candidate a1 is displayed for a displayed X-ray CT image. When the sick portion candidate a2 on the simple X-ray image is interpreted, the X-ray CT image can be also switched to an X-ray CT image including a sick portion candidate corresponding to the sick portion candidate a2 by doubly clicking the mark of the sick portion candidate a2 via the mouse and others. Further, the positions of corresponding CT images may be also displayed by a dotted line and others on the simple X-ray image.

It can be said that in case the sick portion candidate is displayed both on the simple X-ray image and on the X-ray CT image, the possibility of existing as a sick portion is high, however, a case that the sick portion candidate is detected by only either is required to pay attention. For example, referring to FIG. 8, a case that the sick portion candidate c1 is detected on the X-ray CT image, while no corresponding sick portion candidate is detected on the simple X-ray image will be described below. In this case, the doctor is called attention by showing that the following mark is different from lighted marks telling detection on both images by blinking a mark in a position corresponding to the sick portion candidate c1 on the simple X-ray image (a sick portion candidate a3). As the doctor can judge whether the sick portion candidate is a true sick portion or is wrongly detected by comparing the sick portion candidate c1 and the sick portion candidate a3, oversight is reduced that oversight when the doctor judges based upon only either detection result and the reliability is enhanced.

Conversely, referring to FIG. 9, a case that the sick portion candidate a3 is detected on a simple X-ray image, while no corresponding sick portion candidate is detected on an X-ray CT image will be described below. In this case, similarly, on the X-ray CT image, a mark is displayed in a position corresponding to the sick portion candidate a3 on the simple X-ray image, however, as the simple X-ray image has no information in the direction of the y-axis, two parallel lines are displayed in a blinked state and only the direction of the x-axis can be limited as a region having possibility that a sick portion candidate may exist. However, as a sick portion candidate search region is narrowed more than that in case there is no limitation and an elaborate check in the region is enabled, detection efficiency and detection precision are enhanced.

In the case of detection based upon the X-ray CT image, one sick portion candidate may be also detected based upon plural X-ray CT images before and after it depending upon an interval between tomographic images and the size of the sick portion candidate. In this case, to judge whether these sick portion candidates are the same or separate, all related X-ray CT images are required to be checked. However, in contrast with the simple X-ray image, such determination may be relatively facilitated. That is, it can be checked at a glance whether a sick portion ranging over X-ray CT images is one or plural if the sick portion is seen on the simple X-ray image.

Figure 10A:
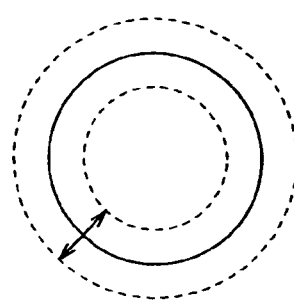
FIG. 10A shows a marker on a simple X-ray image.
Figure 10B:
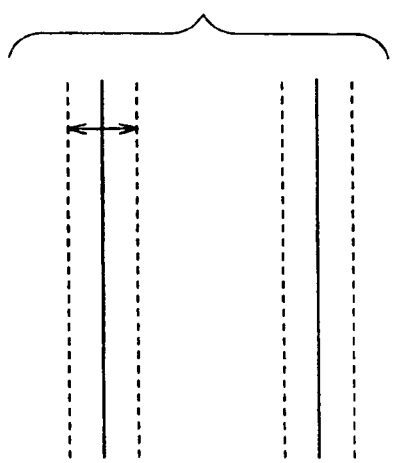
FIG. 10B shows a marker on an X-ray CT image.

A mark showing a sick portion candidate can be also changed in size as shown in FIG. 10. FIG. 10A shows a case that the size of a normal mark is changed and FIG. 10B shows a mark in a case that no corresponding sick portion candidate is detected on an X-ray CT image though the sick portion candidate is detected on a simple X-ray image. In any case, the radius or the width of the mark can be changed by dragging and dropping a part of the mark without the displacement of the center position. Hereby, a mark can also correspond to a case that the interpretation of a shadow in a larger range is desired and a case that the interpretation of a shadow in a focused range is desired.

Further, marks showing sick portion candidates detected according to different algorithm in case plural diseases are examined at a time can be also displayed in different colors. For example, a mark showing a sick portion candidate detected according to algorithm for detecting a lung cancer is displayed in red and a mark showing a sick portion candidate detected according to algorithm for detecting an interstitial lung disease is displayed in yellow.

When the determination of all sick portion candidates on the X-ray CT image is finished, the next X-ray CT image is selected when the interpretation of a shadow is required to be continued (a step S7), control is returned to the step S4, and the determination of lung cancer candidates on the X-ray CT image is repeated (the steps S5 to S7).

In case the interpretation of shadows on all X-ray CT images of the patient "Patient A" is finished and the interpretation of the next patient is continued, control is returned to the step S3 (a step S8) and the operation in the steps S4 to S7 is repeated.

As described above, according to the CAD system 1 equivalent to this embodiment, the reliability of diagnosis based upon an image can be enhanced without imposing an excessive load on a doctor.

In this embodiment, the example that a sick portion candidate is detected based upon an X-ray CT image and a simple X-ray image is described, however, the reliability of diagnosis based upon an image can be also more enhanced than the current reliability by detecting a sick portion candidate based upon only either of an X-ray CT image or a simple X-ray image and superimposing the result of detection on the other image.

Next, referring to the attached drawings, a second embodiment of the CAD system according to the invention will be described.

Figure 11:
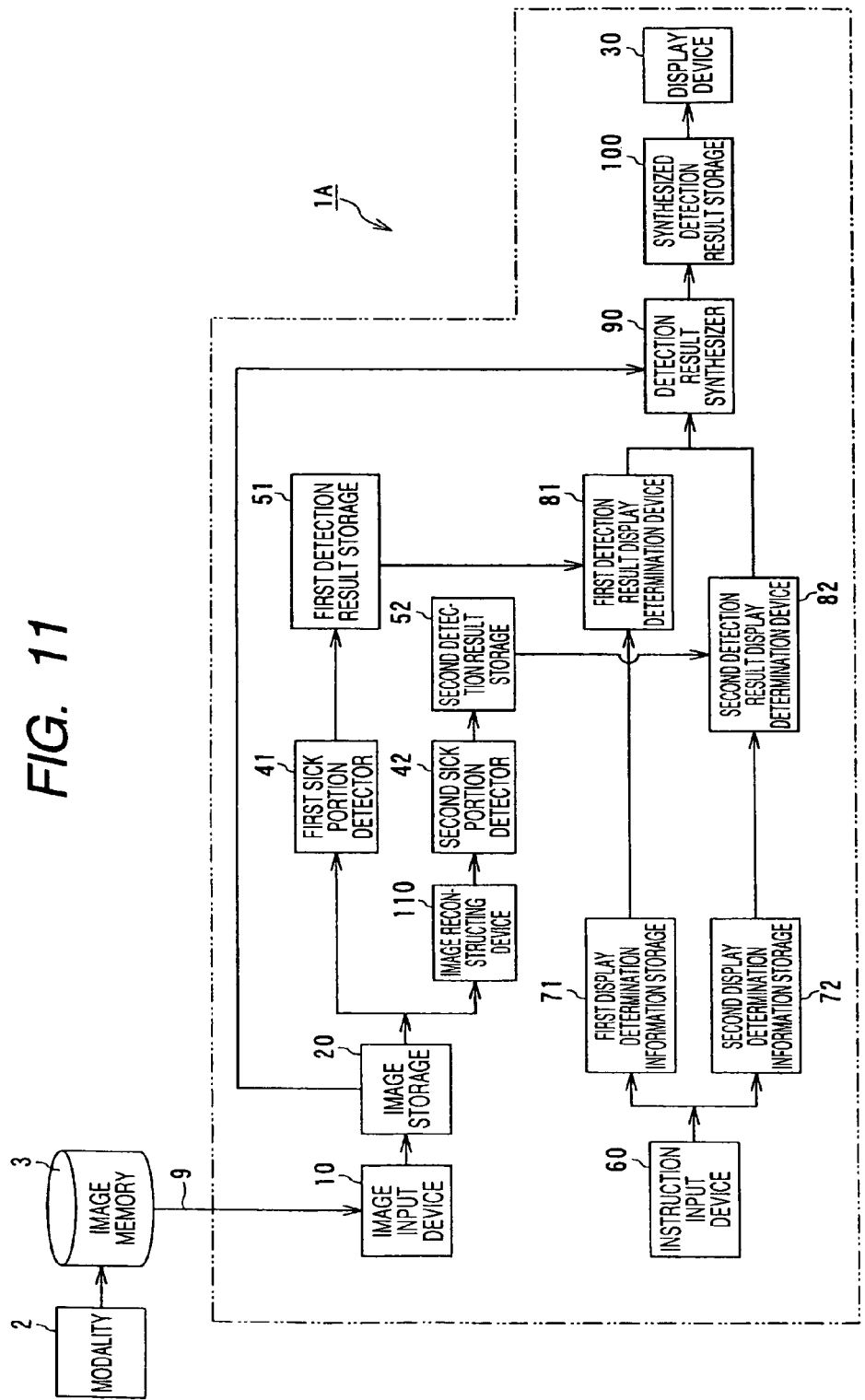
FIG. 11 is a block diagram showing the outline of a function of a computer aided diagnostic system equivalent to a second embodiment of the invention.
Figure 12:
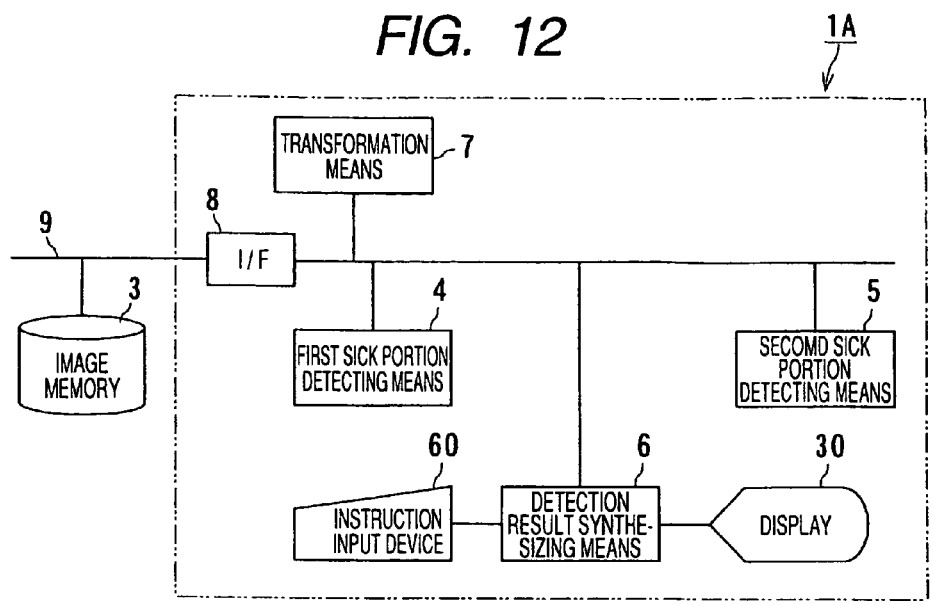
FIG. 12 is a block diagram showing an example of the configuration of the computer aided diagnostic system equivalent to the second embodiment of the invention.

FIG. 11 is a block diagram showing the outline of a function of a CAD system 1A equivalent to the second embodiment and FIG. 12 is a block diagram showing an example of the configuration of the CAD system 1A.

The CAD system 1A equivalent to this embodiment is basically different from that equivalent to the first embodiment in that an image reconstructing device 110 is provided between an image storage 20 and a second sick portion detector 42 as shown in FIG. 11, the other configuration is substantially the same as that in the first embodiment, the same reference numeral is allocated to the same part, and its description is omitted. The image reconstructing device 110 forms image transforming means according to claims. As also clear from FIG. 12, for the configuration of the CAD system 1A, the image transforming means 7 is added to the configuration of the CAD system 1 equivalent to the first embodiment shown in FIG. 2.

In this embodiment, a case that a lung field is doubly checked based upon only multisliced tomographic images acquired by X-ray CT will be described. That is, a digitally reconstructed radiograph in a different direction is generated based upon a tomographic image acquired by X-ray CT and is used in place of a radioscopic image acquired by the other modality as in the first embodiment. If a type of an image in information acquired by one modality is different, algorithm used for detection is also different. Therefore, a different detection result may be acquired and from this point of view, a double check based upon one tomographic image according to different diagnostic rules is significant.

Figure 13:
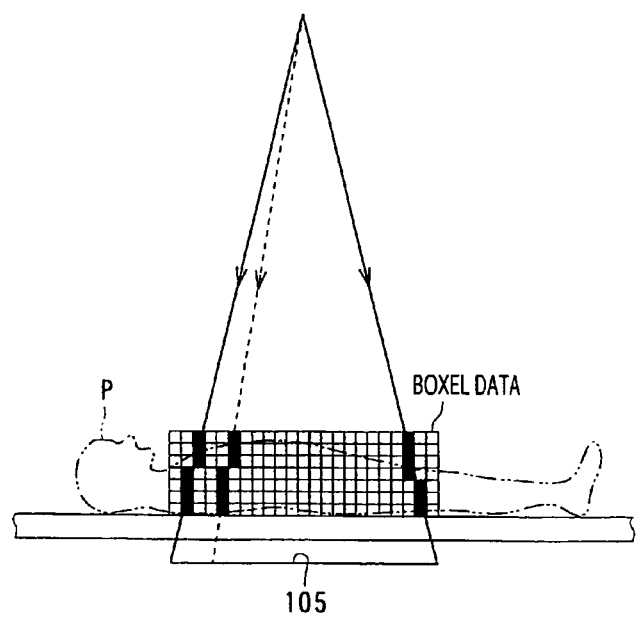
FIG. 13 is an explanatory drawing for explaining a process for calculating a radioscopic image using boxel data.

The image reconstructing device 110 generates a digitally reconstructed radiograph (DRR) from a certain one point based upon a tomographic image acquired by the X-ray CT as shown in FIG. 13. The outline of a procedure is as follows.

First, boxel data which is three-dimensional volume data is generated based upon multiple axial images acquired by the X-ray CT using interpolation. Next, a position of a radiation source is calculated and a radioscopic image based upon the boxel data when a view point is arranged in the calculated position of the radiation source is calculated. For the calculation of the radioscopic image, as shown in FIG. 13, each CT value of boxel data on a path of each beam from the radiation source to a position in which a digitally reconstructed radiograph 105 is formed is added, however, to cope with overflow as a result of addition, suitable normalization is made. In a case according to this embodiment, it is desirable that a view point is located close to a case by an X-ray TV apparatus.

The operation of the CAD system 1A equivalent to this embodiment is also basically different from that equivalent to the first embodiment only in image data transmitted from the image storage 20 to the second sick portion detector 42 and the other configuration is substantially the same as that in the first embodiment. That is, multisliced plural X-ray CT image data stored in the image storage 20 is read according to the control of a controller and a pair of X-ray CT images are respectively sent to both a first sick portion detector 41 and the image reconstructing device 110. In the image reconstructing device 110, as described above, a radiograph is digitally reconstructed and the acquired digitally reconstructed radiograph is sent to the second sick portion detector 42 for analysis. The digitally reconstructed radiograph is also returned to the image storage 20 and may be also stored in it so that second digital reconstruction is not required.

The operation for interpreting a shadow using the CAD system 1A of a doctor can be performed as in the first embodiment because the CAD system 1A is configured and operated as described above.

In this embodiment, the case that DRR is generated based upon axial images and a sick portion is searched according to different algorithm for respective images is described, however, a projective image is not limited to DRR and for a transformed example, a multi planar reconstruction (MPR) image the section of which is different from that of an axial image, particularly a coronal image and an oblique image can be also applied in place of DRR. In this case, in place of the image transforming means 7, image reconfiguring means is provided.

MPR means extracting an arbitrary plane from stereoscopic image data using the data acquired by a tomographic image imaging device and displaying the section. FIG. 14 show heads as an example. As shown in FIGS. 14A and 14B, generally, the position of a one-side section is determined by indicating by a line ROI on a two-dimensional image such as an axial image, a sagittal image and a coronal image. For example, a line ROI1 or a line ROI2 is determined on an axial image shown in FIG. 14A and a section corresponding to the line ROI1 for example is displayed as shown in FIG. 14C. A line ROI3 is determined on a coronal image shown in FIG. 14B and a section corresponding to the line ROI 3 is displayed as shown in FIG. 14D.

The above-mentioned embodiments are embodiments for explanation and do not limit the scope of the invention. Therefore, person skilled in the art can adopt embodiments acquired by replacing each element of these embodiments or the whole elements with an embodiment equivalent to these embodiments, however, these embodiments are also included in the scope of the invention.

INDUSTRIAL APPLICABILITY

As described above, as the image diagnosis aiding system according to the invention is provided with the function for displaying a sick portion candidate detected based upon an image acquired by a first modality on an image acquired by a second modality and a function for conversely displaying a sick portion candidate detected by the second modality on an image acquired by the first modality, the oversight of the sick portion can be prevented.

Besides, in the invention, effect that as the invention is provided with a function for transforming a tomographic image acquired by one modality to a projective image and displaying a sick portion candidate detected based upon the tomographic image on the projective image, the double check of the sick portion based upon only the image acquired by one modality is enabled is acquired.

The invention claimed is:
1. A computer aided diagnostic system, comprising:
a processor configured to
    detect a cancer candidate by automatically extracting a field of interest based upon a simple X-ray image acquired by a simple X-ray device, and extracting the cancer candidate in the field of interest, the simple X-ray image being defined over a first direction and a second direction perpendicular to the first direction;
    automatically determine whether a sick portion candidate corresponding to the cancer candidate exists in any of a plurality of X-ray CT images acquired by an X-ray CT device and corresponds to a position of the detected cancer candidate; and
    cause a marker extending in a third direction intersecting with the first and second directions to be displayed on a displayed X-ray CT image when it is determined that the sick portion candidate corresponding to the cancer candidate does not exist in any of the X-ray CT images, the marker indicating a region in which a sick portion candidate might exist.
2. The computer aided diagnostic system according to claim 1, wherein the cancer candidate is a lung cancer candidate and the field of interest is a lung field.
3. The computer aided diagnostic system according to claim 1, wherein the marker is a pair of parallel lines.
4. The computer aided diagnostic system according to claim 1, wherein the third direction is perpendicular to the first and second directions.
5. A computer aided diagnostic system, comprising:
a processor configured to
    detect a first cancer candidate by automatically extracting a first field of interest based upon a simple X-ray image of a subject acquired by a simple X-ray device, and extracting the first cancer candidate in the first field of interest, the simple X-ray image being defined over a first direction and a second direction perpendicular to the first direction;

attempt to detect a second cancer candidate in a second field of interest based upon an X-ray CT image of a plurality of X-ray CT images related to a same region of interest of the same subject acquired by an X-ray CT device; and compare the results of detection of the first detecting and second attempt of detecting and determine automatically whether the second cancer candidate was detected in any of the X-ray CT images, wherein when it is determined that the second cancer candidate was not detected in any of the X-ray CT images, a marker extending in a third direction intersecting with the first and second directions is displayed on a displayed X-ray CT image, the marker indicating a region in which a sick portion candidate might exist.

6. The computer aided diagnostic system according to claim 5, wherein the processor is further configured to cause a display to display a detected portion so that the detected portion can be identified, when the processor judges that the detected portion is detected as a cancer candidate by only one of the first detecting and second attempt of detecting.

7. A computer aided diagnosing method, comprising:

detecting a cancer candidate by automatically extracting a field of interest based upon a simple X-ray image acquired by a simple X-ray device, and extracting the cancer candidate in the field of interest, the simple X-ray image being defined over a first direction and a second direction perpendicular to the first direction;

automatically determining whether a sick portion candidate corresponding to the cancer candidate exists in any of a plurality of X-ray CT images acquired by an X-ray CT device and corresponds to a position of the detected cancer candidate; and displaying a marker extending in a third direction intersecting with the first and second directions on a displayed X-ray CT image when it is determined that the sick portion candidate corresponding to the cancer candidate does not exist in any of the X-ray CT images, the marker indicating a region in which a sick portion candidate might exist.

8. A computer aided diagnosing method, comprising:

detecting a first cancer candidate by automatically extracting a first field of interest based upon a simple X-ray image of a subject acquired by a simple X-ray device, and extracting the first cancer candidate in the first field of interest, the simple X-ray image being defined over a first direction and a second direction perpendicular to the first direction;

attempting to detect a second cancer candidate in a second field of interest based upon an X-ray CT image of a plurality of X-ray CT images related to a same region of interest of the same subject acquired by an X-ray CT device; and comparing the results of detection of the first detecting and second attempt of detecting and automatically determining whether the second cancer candidate was detected in any of the X-ray CT images, wherein when it is determined that the second cancer candidate was not detected in any of the X-ray CT images, displaying a marker extending in a third direction intersecting with the first and second directions on a displayed X-ray CT image, the marker indicating a region in which a sick portion candidate might exist.

9. The computer aided diagnosing method according to claim 8, further comprising:

displaying a mark when a cancer candidate is detected on only one image among the simple X-ray image and the X-ray CT image that is different from marks respectively displayed when the first and second cancer candidates are detected on both images.

10. The computer aided diagnostic system according to claim 5, wherein the processor is further configured to cause a mark to be displayed when a cancer candidate is detected on only one image among the simple X-ray image and the X-ray CT image that is different from marks respectively displayed when the first and second cancer candidates are detected on both images.

* * * * *